(12) United States Patent
Zheng et al.

(10) Patent No.: US 12,226,785 B2
(45) Date of Patent: Feb. 18, 2025

(54) VACUUM CHAMBER STRUCTURE OF ULTRA-HIGH GRAVITY GEOTECHNICAL CENTRIFUGE DEVICE

(71) Applicant: ZHEJIANG UNIVERSITY, Zhejiang (CN)

(72) Inventors: Chuanxiang Zheng, Zhejiang (CN); Weian Lin, Zhejiang (CN); Bingbing Chen, Zhejiang (CN); Jianqun Jiang, Zhejiang (CN); Yunmin Chen, Zhejiang (CN); Liming Tang, Zhejiang (CN); Jiao Lin, Zhejiang (CN); Danyang Dou, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 935 days.

(21) Appl. No.: 16/981,691

(22) PCT Filed: May 31, 2019

(86) PCT No.: PCT/CN2019/089466
§ 371 (c)(1),
(2) Date: Sep. 16, 2020

(87) PCT Pub. No.: WO2020/220428
PCT Pub. Date: Nov. 5, 2020

(65) Prior Publication Data
US 2023/0102671 A1 Mar. 30, 2023

(30) Foreign Application Priority Data

Apr. 28, 2019 (CN) .......................... 201910350086.3

(51) Int. Cl.
*B04B 15/02* (2006.01)

(52) U.S. Cl.
CPC .................................. *B04B 15/02* (2013.01)

(58) Field of Classification Search
CPC .............................. B04B 15/02; G01N 33/24
See application file for complete search history.

*Primary Examiner* — Walter D. Griffin
*Assistant Examiner* — Shuyi S. Liu
(74) *Attorney, Agent, or Firm* — W&G Law Group

(57) ABSTRACT

A vacuum chamber structure of an ultra-high gravity geotechnical centrifuge device, comprising: a cylindrical shell, a convex head, a bottom head, a lower bearing sealing cover, and a vacuum pressure-bearing chamber formed by sealing a top cylindrical cylinder and an upper sealing plate with sealing rings; wherein a high-speed rotor system is enclosed in the vacuum pressure-bearing chamber, and a cylindrical cooling device is installed between an internal side of the cylindrical shell and the high-speed rotor system. An annular cooling device is provided directly above the hanging baskets on both sides of the centrifuge arm. A vibration isolation expansion joint is arranged at the intersection of the high-speed rotor system and the cylindrical cylinder, which isolates the vibration of the main engine from the vacuum chamber and greatly reduces the vibration.

7 Claims, 4 Drawing Sheets

VACUUM CHAMBER STRUCTURE OF ULTRA-HIGH GRAVITY GEOTECHNICAL CENTRIFUGE DEVICE

BACKGROUND OF THE PRESENT INVENTION

Field of Invention

The present invention relates to a vacuum chamber structure, and more particularly to a vacuum chamber structure of an ultra-high gravity geotechnical centrifuge device.

Description of Related Arts

High-acceleration, high-speed geotechnical centrifuge is an indispensable device for the study of geological evolution process reproduction experiments such as rock and soil evolution, geological structure evolution, and geological disaster reduction. Vibration and heat dissipation are two outstanding problems of ultra-high gravity machines and geotechnical centrifuges. Vibration will cause fatigue damage to the structure, and heat generation will cause the temperature in the cabin to rise and cause it to fail to work properly. With the continuous increase of acceleration g, the heat dissipation problem of the geotechnical centrifuge itself becomes a problem, because the higher the rotation speed and linear speed of the centrifuge, the greater the heat generated by the friction between the rotating arm, the hanging basket and the air. When the acceleration is below 500 g, it can generally be cooled by a chiller unit or by natural air circulation. But when the acceleration increases to more than 1000 g, or even more than 1500 g, the heat produced in the centrifugal cabin with a diameter of 11 meters can reach 10 MW, which is equivalent to the heat exchange of a large air conditioning unit of 50,000 square meters; and such a huge heat exchange requires a huge air volume. And too much wind will affect the vibration of the rotating arm, so conventional cold air cooling can no longer meet the heat dissipation needs of high-acceleration centrifuges. If the temperature control is not solved well, all the instruments in the centrifuge cabin will have problems. Generally, the temperature control of the centrifuge cabin is required below 45° C. Cooling is generally combined with cold water cooling around the centrifugal cabin wall. However, when the load of the centrifuge further increases, the heat production in the centrifuge chamber will further increase. At this time, cold air cooling combined with cold water cooling cannot meet the heat dissipation requirements. In order to solve this problem, the most effective method is to vacuumize the centrifugal chamber and reduce the density of the air to reduce the friction and heat generation between the rotating arm and the air. However, vacuuming will cause other problems. One is that the air molecules are thin under vacuum. The heat transfer capacity is also greatly reduced, and the air cannot be convective in the vacuum state. Therefore, the heat caused by the friction between the rotating arm and the air cannot be effectively transferred to cold wall, hence result in temperature increasing of the rotating arm. Another problem is that the bearings of the centrifuge under high vacuum will leak oil, and the sealing around the centrifuge cabin becomes difficult, so the vacuum degree cannot be too high.

At present, the patents related to the heat dissipation of the geotechnical centrifuge test chamber mainly include CN201210056367.6 Spray water curtain cooling device for the geotechnical centrifuge test chamber by Liu Guogui etc., Zhejiang University, which proposes a method of spraying cooling water around the centrifuge chamber wall. The method of heat dissipation is very effective, but when the acceleration increases to more than 1000 g, water cooling alone cannot achieve the purpose of heat dissipation and temperature control. Cold air cooling is a conventional technology, and the natural air cooling uses the air flow field of the centrifuge itself to achieve circulation cooling, other cooling and heat dissipation technologies have not been reported.

SUMMARY OF THE PRESENT INVENTION

In order to solve the problems of oil leakage in the bearing system of the ultra-high acceleration geotechnical centrifuge and vibration of the main engine, vacuuming of the main engine room is a good choice. The purpose of the present invention is to provide a vacuum chamber structure of an ultra-high gravity geotechnical centrifuge with a bearing on the top. The system greatly enhances the rigidity of the high-speed rotor, reduces the vibration of the main engine, isolates the bearing system outside the vacuum cavity through a special method, and completely solves the problem of oil leakage. A special vibration isolation device is adopted to isolate the vibration of the main engine from the vacuum cavity to achieve requirements for safe operation. The built-in heat dissipation technology, the snake-shaped curved runners to increase the heat dissipation efficiency, the curved panel heat exchangers are utilized to ensure that the wind resistance power of the inner wall does not change, so as to achieve the purpose of low energy consumption and reliable temperature control. A bearing system provided on the top makes the rigidity of high speed rotor greatly enhanced, reducing the vibration of the host.

In order to achieve the above-mentioned purpose of the invention, the technical solution adopted by the present invention is as follows.

A vacuum chamber structure of an ultra-high gravity geotechnical centrifuge device, comprising: a cylindrical shell, a convex head, a bottom head, a lower bearing sealing cover, and a vacuum pressure-bearing chamber formed by sealing a top cylindrical cylinder and an upper sealing plate with sealing rings;

wherein a high-speed rotor system is enclosed in the vacuum pressure-bearing chamber, and a cylindrical cooling device is installed between an internal side of the cylindrical shell and the high-speed rotor system, and a lower end of the main shaft of the high-speed rotor system extends through the lower bearing sealing cover and a lower bearing system, extends out of the bottom head, and respectively connects a coupling and a motor, in such a manner that the lower bearing system, the coupling and the motor are isolated from a vacuum pressure chamber;

wherein an upper end of the main shaft of the high-speed rotor system passes through the upper sealing plate and the upper bearing system to connect an instrument compartment installed in the top cylindrical cylinder; in such a manner that the upper bearing system and the instrument compartment in the top cylindrical cylinder at the center of the convex head are isolated from the vacuum pressure chamber;

wherein an upper bearing system support device is a radial support structure formed by an upper bearing ring and a plurality of beams; a first end of each beams is connected to the upper bearing support ring, and a second end of the beams passes through the cylindrical shell and is connected to the connecting backing plate; each connecting backing plate is then connected to the side concrete, the upper bearing system is installed in the upper bearing support ring; a first end of the multiple beams is surrounded by a beam vibration isolation device, the cross-opening of a periphery of one end of the multiple beams and the cylindrical shell is a clearance fit with beam passing, each of the multiple beams is connected in seal with the cylindrical shell via a beam vibration isolation device and a gasket;

wherein hanging baskets are respectively provided on both sides of the rotating arm of the centrifuge in the high-speed rotor system, and an annular cooling device is provided on each beam directly above the hanging basket;

a cylindrical shell is provided with multiple side wall connector pipes and a side door; the convex head is provided with a vacuum exhaust pipe, a lifting hole, an air intake pipe, and a vacuum recompression pipe; and a spare connection pipe;

the cylindrical cooling device and the annular cooling device are connected and communicated to the upper liquid collecting pipe and the lower liquid collecting pipe, and the upper liquid collecting pipe passes through the cylindrical shell to connect the low-temperature outlet of the refrigerator, and the lower liquid collecting pipe passes through the cylindrical shell to connect the return water inlet of the refrigerator; and a side door is opened on a side of the cylindrical shell.

The top cylindrical cylinder is provided with one or more U-shaped or Ω-shaped vibration isolation devices in a middle of a body of the top cylindrical cylinder, and an upper end of the top cylindrical cylinder and convex head is connected through a block flange and the sealing ring, the lower end of the top cylindrical cylinder is connected with the upper bearing support ring through another sealing ring, and the bottom of the upper bearing support ring is sealed and connected with the upper sealing plate, the upper sealing plate is dynamically sealed and connected with the main shaft.

The beam vibration isolation device comprises a beam cylindrical sleeve and one or more U-shaped or Ω-shaped vibration isolation expansion joints provided in the middle of the body of the beam cylindrical sleeve; a first end of the beam vibration isolation device is welded or connected to the beam through a first gasket, and a second end of the beam vibration isolation device is connected to the cylindrical shell through a second gasket.

The cylindrical cooling device comprises multiple arc-shaped cooling units assembled into a complete circular cylinder, and each of the cooling unit comprises an upper side plate and a liquid inlet pipe welded to the upper plate, a lower side plate, an outer arc plate and an inner arc plate, a left side plate, a right side plate and an outlet pipe welded to the lower side plate which form a closed cavity; wherein the upper side plate, the lower side plate, the left side plate, and the right side plate are in shapes of arc-shaped partitions, all of which are plates with an external convex arc-shape and an inner concave arc-shape; the outer arc plate and the inner arc plate are welded to the left side plate and the right side plate by a plurality of curved baffles, forming an S-shaped flow path; the liquid inlet pipe is connected and communicated with the upper liquid collecting pipe, and the water outlet pipe is connected and communicated with the lower liquid collecting pipe; an annular cooling device comprises several segment of ring cooling units, which form a complete circular ring plate.

The bottom head is welded or riveted and fixed on the bottom concrete by a tie bar embedded in the bottom concrete; the bottom head is welded to a bottom end of the cylindrical shell to form one body.

The upper bearing system is supported by the upper bearing support ring and multiple beams with one end fixed on the upper bearing support ring and another end connected with the connecting backing plate, and the connecting backing plate is fixed on the side concrete.

Materials of the cylindrical cooling device and the annular cooling device are aluminum alloy, stainless steel or low carbon steel.

The beneficial effects of the present invention are as follows.

(1) Since the bearing system is placed outside the vacuum chamber, it can be operated under high vacuum to solve the problem of oil leakage in the current high-speed rotor bearing system under vacuum.

(2) Placing the heat dissipation device inside the vacuum chamber can further improve the heat transfer coefficient and increase the heat dissipation effect.

(3) Different from the traditional geotechnical centrifuge using a single-bearing cantilever beam rotor, the high-speed rotor of the present invention is equipped with a top bearing system, which greatly increases the stiffness and operational stability of the high-speed rotor, and solves the problem of high-speed rotor vibration.

(4) At the intersection of the high-speed rotor system and the cylindrical shell, one or more U-shaped or Ω-shaped vibration isolation expansion joints are used to isolate the vibration of the main machine from the vacuum chamber and greatly reduce the vibration.

(5) Using one or more U-shaped or Ω-shaped vibration isolation expansion joints between the upper bearing support ring and the convex head to isolate the vibration of the upper bearing system from the vacuum chamber, and at the same time, the deformation of the convex head and upper bearing system is separated.

Therefore, using this inventing technology, the temperature in the centrifugal cabin can be controlled below 45° C. when the acceleration increases to more than 1500 g.

In the Figures, 1—motor, 2—coupling, 3—lower bearing system, 4—lower bearing seal cover, 5—tie bar, 6—bottom concrete, 7—bottom head, 8—side concrete, 9—lower liquid collecting pipe, 10—cylindrical shell, 11—cylindrical cooling device, 12—main shaft, 13—hanging basket, 14—centrifuge arm, 15—lower sealing flange, 16—upper sealing flange, 17—tighting device, 18—upper bearing system, 19—convex head, 20—vibration isolation device, 21—vacuum exhaust pipe, 22—upper sealing plate, 23—sealing ring, 24—top cylindrical cylinder, 25—instrument compartment, 26—upper bearing system support device, 27—annular cooling device, 28—upper liquid collecting pipe, 29—lifting hole, 30—beam vibration isolation device, 31—sealing gasket, 32—beam, 33—upper bearing support ring, 34—intake pipe, 35—vacuum recompression pipe, 36—outer arc plate, 37—inner arc plate, 38—upper side plate, 39—liquid inlet pipe, 40—curved baffle, 41—right side plate, 42—S-shaped flow path, 43—left side plate, 44—outlet pipe, 45—connecting backing plate, 46—high-speed rotor system, 47—vibration isolation expansion joint, 48—gasket, 49—connecting plate, 50—block flange, 51—side wall connection pipe, 52—side door, 53—spare connection pipe, 54—beam cylindrical sleeve, 55—bottom side plate, 56—segment of ring cooling unit.

DETAILED DESCRIPTION OF THE PREFERRED EMBODIMENT

The present invention will be further described below with reference to the drawings and embodiments.

Figure 1:
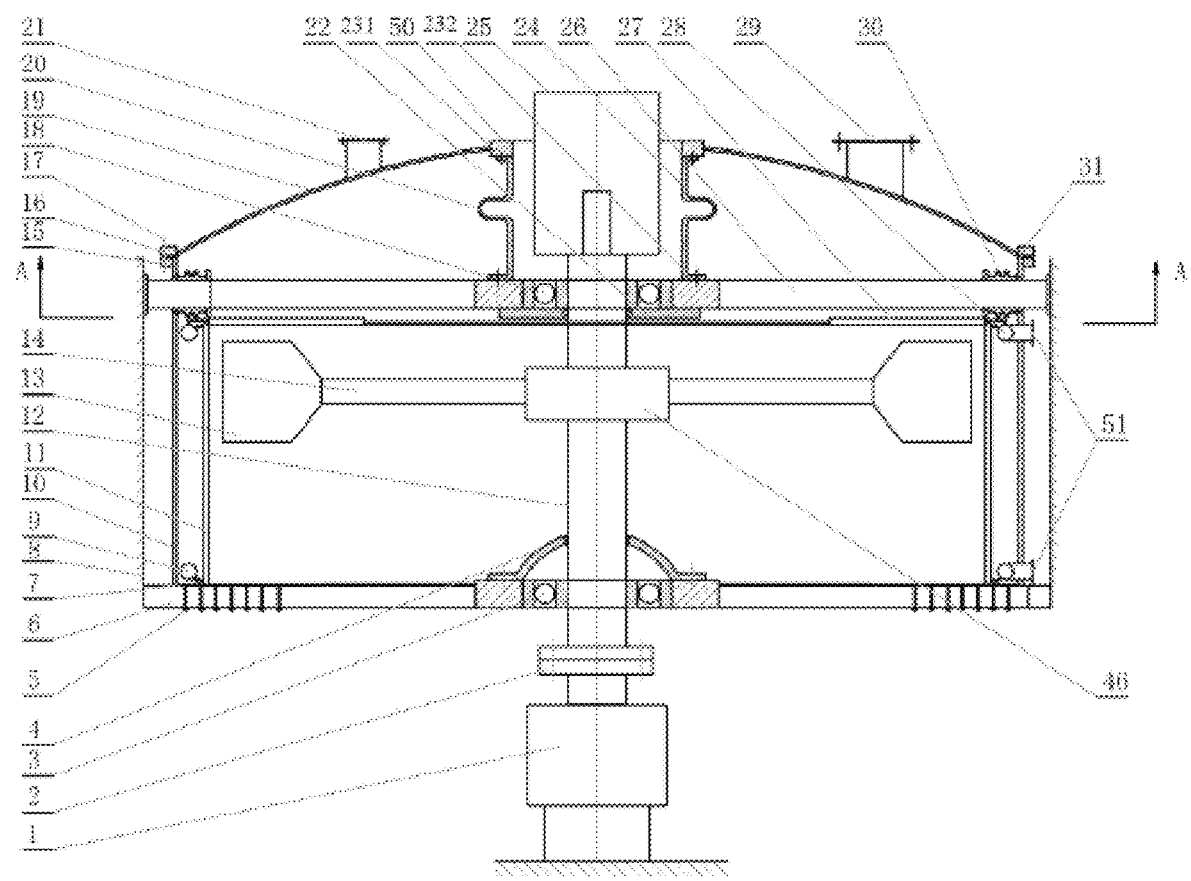
FIG. 1 is a front sectional view of the structure of the present invention.
Figure 2:
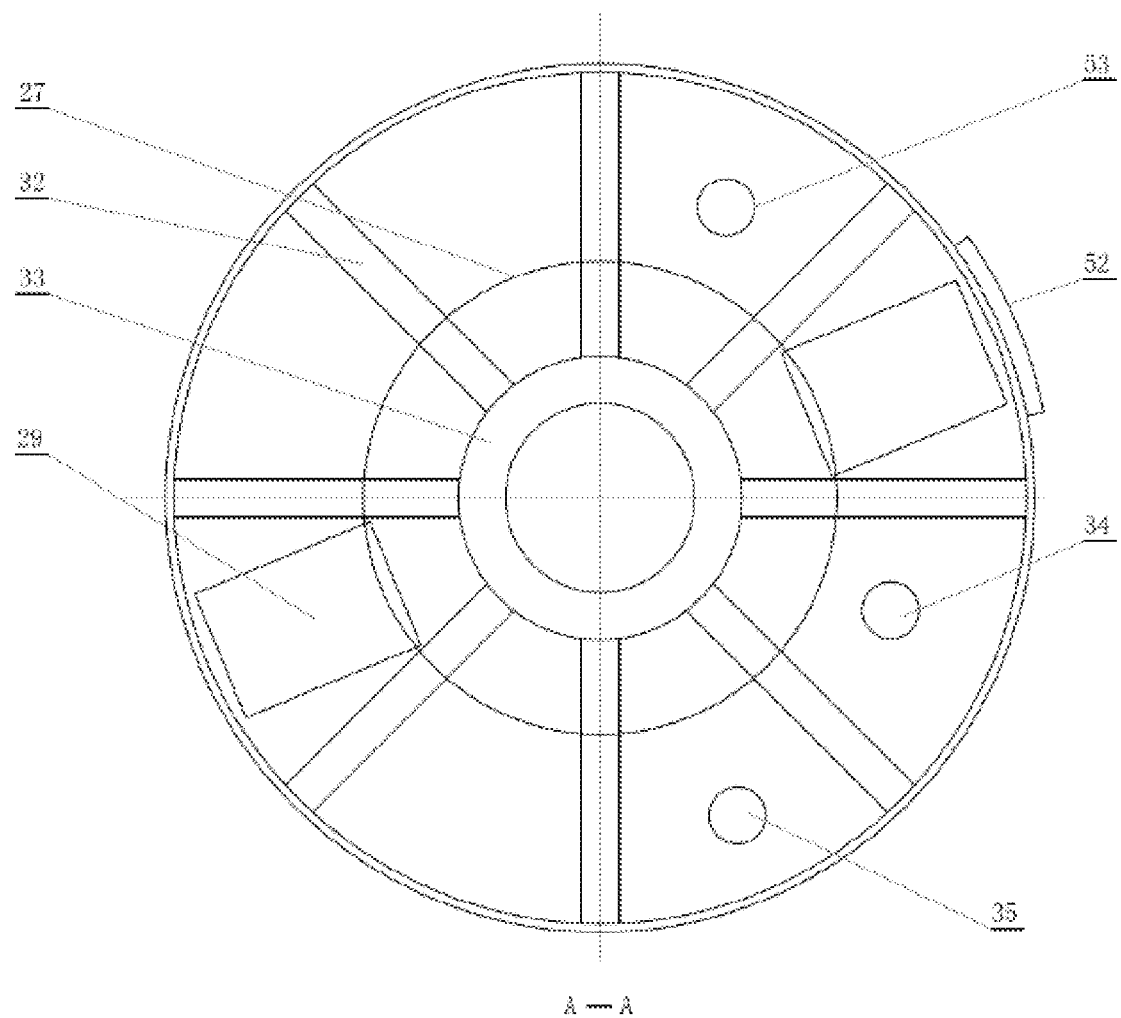
FIG. 2 is an A-A cross-sectional view of FIG. 1.

As shown in FIGS. 1 and 2, the present invention comprises a cylindrical shell 10, a convex head 19, a bottom head 7, a lower bearing sealing cover 4, a top cylindrical cylinder 24, and an upper sealing plate 22, a lower sealing flange 15, and an upper sealing flange 16, a sealing gasket 31 provided between the two flanges are detachably sealed by the tighting device 17 to form a vacuum pressure-bearing cavity; an upper end of the cylindrical shell 10 is connected with an upper bearing system support device 26 and a convex head 19, wherein the convex head 19 is located above the upper bearing system support device 26, the convex head 19 and the upper bearing system support device 26 are connected by the top cylindrical cylinder 24. A lower end of the cylindrical shell 10 is connected with the lower head 7 and the lower bearing sealing cover 4. A main shaft 12 of the centrifuge is sleeved in a central inner hole of the upper bearing system support device 26 and the lower bearing sealing cover 4, and the upper end of the cylindrical shell 10 is fixedly connected with the lower sealing flange 15. The lower end of the outer ring of the convex head 19 is fixedly connected with the upper sealing flange 16, and the lower sealing flange 15 and the upper sealing flange 16 are sealed and fixed, so that an upper end of the cylindrical shell 10 and the convex head 19 are sealed and fixedly connected.

The high-speed rotor system 46 is enclosed in the vacuum pressure-bearing cavity. A cylindrical cooling device 11 is installed between the inner side of the cylindrical shell 10 and the high-speed rotor system 46. A lower end of the main shaft 12 of the high-speed rotor system 46 passes through the lower bearing cover 4 and the lower bearing system 3, extends the out of the bottom head 7, and connects the coupling 2 and the motor 1 in sequence. The main shaft 12 is sleeved in the central bore of the lower head 7 through the lower bearing system 3. The lower bearing system 3 is axially positioned and installed to isolate the lower bearing system 3, the coupling 2 and the motor 1 are isolated from the vacuum pressure chamber; the upper end of the main shaft 12 of the high-speed rotor system 46 passes through the upper sealing plate 22 and the upper bearing system 18 to connect the instrument compartment 25 installed in the top cylindrical cylinder 24; so as to isolate the upper bearing system 18 and the instrument compartment 25 in the top cylindrical cylinder 24 at the center of the convex head 19 out of the vacuum pressure chamber.

The upper bearing system support device 26 comprises an upper bearing support ring 33 and a plurality of beam 32, with eight beams in FIG. 2, forming a radial support structure. A first end of each of the beam 32 is connected to the upper bearing support ring 33, and a second end of the beam 32 passes through the cylindrical shell 10 to connect the connecting backing plate 45, and each of the connecting backing plate 45 is connected to the side concrete 8. The upper bearing system 18 is installed in the upper bearing support ring 33; the circumference of one end of the multiple beam 32 is cylindrical cross opening of the cylinder 10 is a clearance fit, that is, the cross opening has a gap of less than 10 mm. Each beam 32 is connected to the cylindrical shell 10 by a gasket 48 through a beam isolation device 30 respectively.

Hanging baskets 13 are installed on both sides of the centrifuge arm 14 of the high-speed rotor system 46, and an annular cooling device 27 is provided on each beam 32 directly above the hanging basket 13.

As shown in FIG. 2, the cylindrical shell 10 is provided with a plurality of side wall connection pipe 51 and a side door 52, and the convex head 19 is provided with a vacuum exhaust pipe 21, a lifting hole 29, an air inlet pipe 34, and a vacuum recompression pipe 35 and a spare connection tube 53; wherein the cylindrical cooling device 11 and the annular cooling device 27 are both in communication with the upper liquid collecting pipe 28 and the lower liquid collecting pipe 9, and the upper liquid collecting pipe 28 passes through the cylindrical barrel 10 through the respective side wall connection pipe 51 to be connected to the low-temperature outlet of the refrigerator, the lower liquid collecting pipe 9 passes through the cylindrical shell 10 and is connected to the return water inlet of the refrigerator via respective side wall connection pipe 51; a side door 52 is opened on the side of the cylindrical shell 10.

As shown in FIGS. 1 and 2, one or more U-shaped or Ω-shaped vibration isolation devices 20 in the middle portion of the cylindrical cylinder body is provided on the top of the cylindrical cylinder 24. The middle part of the top cylindrical cylinder 24 bends the wall of the top cylindrical cylinder 24 into a circular U-shaped or Ω-shaped structure, and the upper end of the top cylindrical cylinder 24 and the convex head 19 is connected in seal to the sealing ring 23 by a block flange 50, wherein the block flange 50 is sealed to the inner ring of the convex head 19, the lower end of the block flange 50 is connected to the upper end of the top cylindrical cylinder 24 by the sealing ring 23, the lower end of the top cylindrical cylinder 24 and the upper bearing support ring 33 are hermetically connected through another sealing ring 23, and the bottom of the upper bearing support ring 33 is hermetically connected with the main shaft 12 after being hermetically connected with the upper sealing plate 22.

Figure 5:
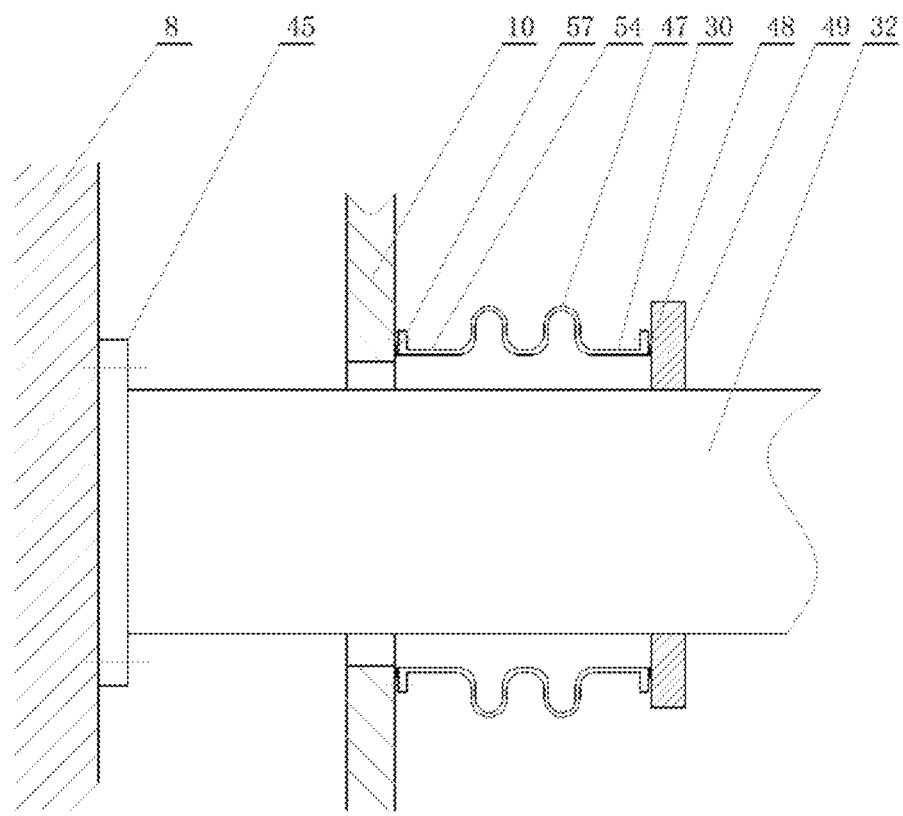
FIG. 5 is a connection diagram of a beam anti-vibration isolation device.

As shown in FIGS. 2 and 5, the beam vibration isolation device 30 comprises a beam cylindrical sleeve 54 and one or more U-shaped or Ω-shaped vibration isolation expansion joints 47 located in the middle of the beam cylindrical sleeve 54. The vibration isolation expansion joint 47 is installed in the middle part of the beam cylindrical sleeve 54 and the cylinder wall of the beam cylindrical sleeve 54 is bent into a circular U-shaped or Ω-shaped structure. A first end of the beam vibration isolation device 30 is welded or connected to the beam 32 in a sealed manner by the gasket 48 and the connecting plate 49. Specifically, the gasket 48 is first connected to the annular connecting plate 49. The annular connecting plate 49 is then sealed and sleeved outside the beam 32, and the second end of the beam vibration isolation device 30 is sealed by the gasket 48 connected to the cylindrical shell 10.

Figure 3:
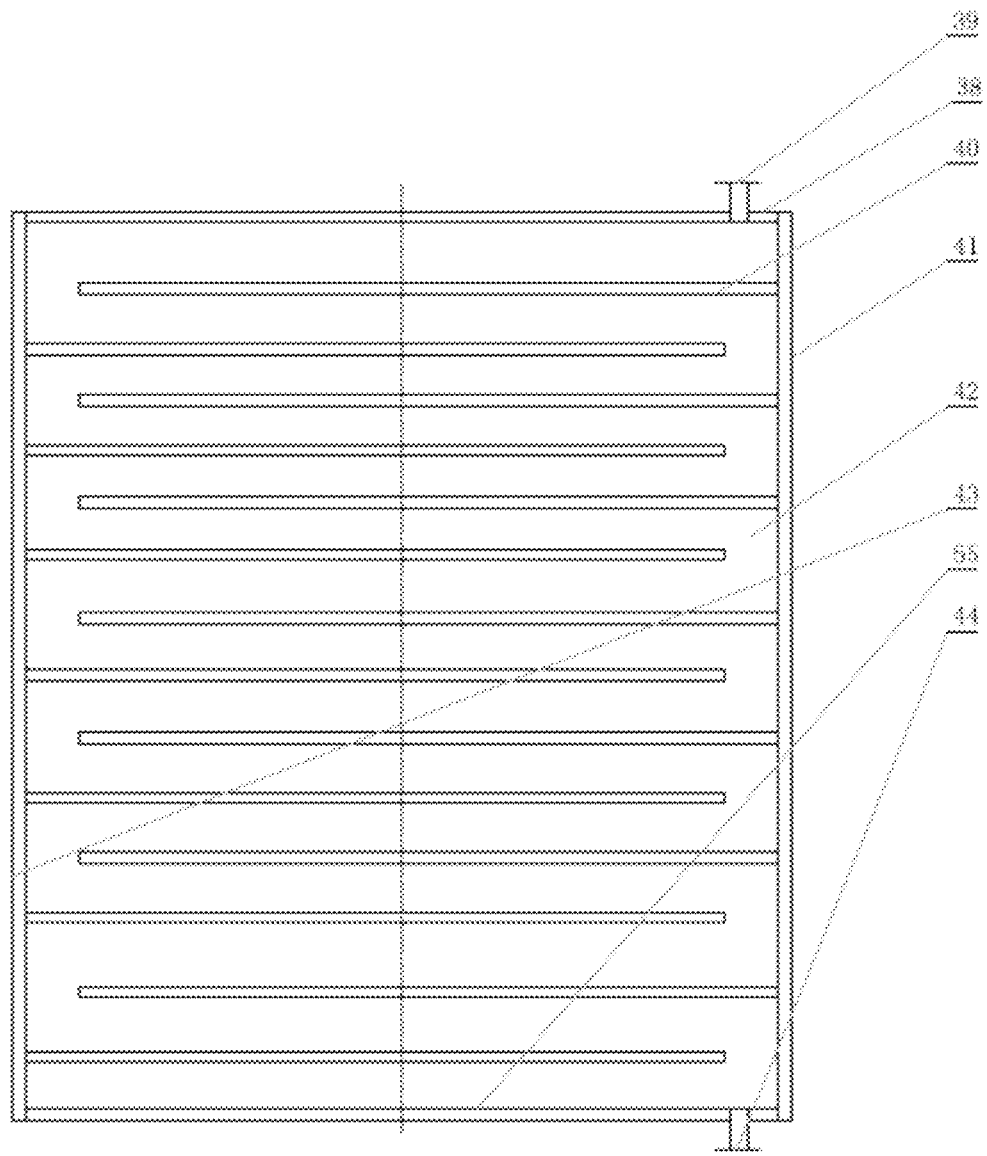
FIG. 3 is a structural diagram of a cylindrical cooling device unit.
Figure 4:
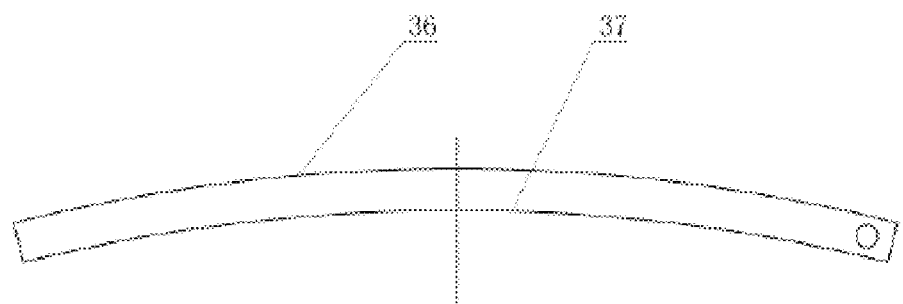
FIG. 4 is a top view of a cylindrical cooling device unit.
Figure 6:
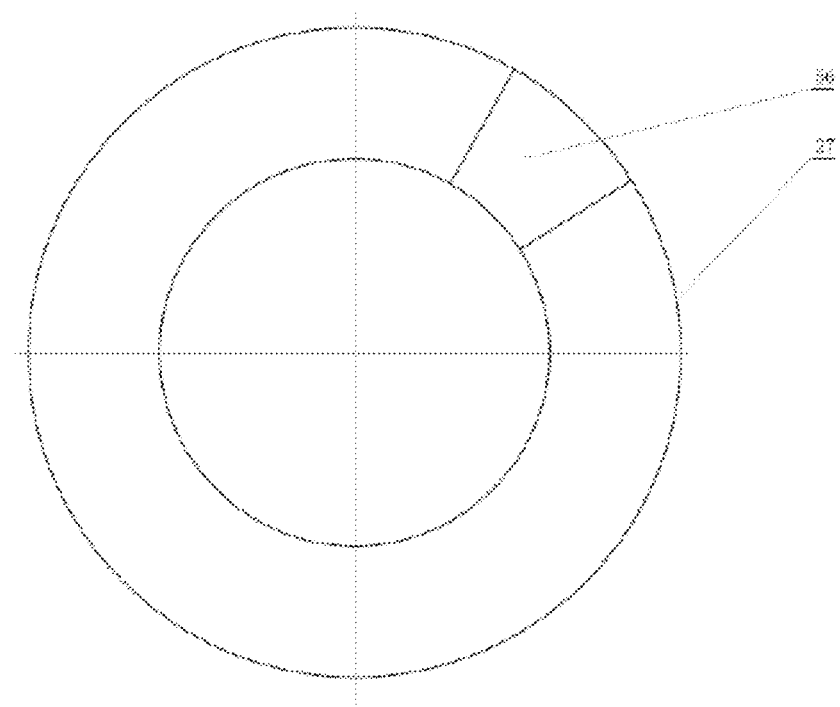
FIG. 6 is a schematic diagram of a circular cooling device

As shown in FIGS. 3, 4, and 6, the cylindrical cooling device 11 comprises: a plurality of arc-shaped cylindrical cooling units assembled into a complete circular cylinder, and each of the plurality of the cooling unit comprises of an upper side plate 38, a liquid inlet pipe 39 welded to the upper side plate 38, a lower side plate 55, an outer plate 36 and an inner plate 37, a left side plate 43, a right side plate 41 and a liquid outlet pipe 44 welded to the lower side plate 55 form one sealed cavity; the upper side plate 38, the lower side plate 55, the left side plate 43, and the right side plate 41 are in shapes of arc partitions, all of which are plates with a convex arc on the outer ring and a concave arc on the inner ring. The plate 36 and the inner plate 37 are welded to the left side plate 43 and the right side plate 41 through a plurality of arc-shaped baffles 40 alternately to form an S-shaped flow path 42 which is arranged along the axis of the cylinder; the liquid inlet pipe 39 is communicated with the upper liquid collecting pipe 28, and the liquid outlet pipe 44 is communicated with the lower liquid collecting pipe 9. The annular cooling device 27 is similar in structure to the cylindrical cooling device 11, and is mainly composed of a plurality of arc shape plane segment of ring cooling unit 56. The S-shaped flow channel is arranged in a radial direction of the segment of ring cooling unit 56, and the liquid inlet and outlet pipes are respectively communicated with the upper liquid collecting pipe 28 and the lower liquid collecting pipe 9.

As shown in FIGS. 2 and 5, the lower head 7 is fixed to the bottom concrete 6 by welding or riveting with tie bar 5 embedded in the bottom concrete 6. The bottom head 7 is welded to the bottom end of the cylindrical shell 10 into one body.

The upper bearing system 18 is supported by the upper bearing support ring 33 and multiple beams 32 with one end fixed on the upper bearing support ring 33 and another end connected with the connecting backing plate 45, and the connecting backing plate 45 is fixed on the side concrete 8.

The materials of the cylindrical cooling device 11 and the annular cooling device 27 are materials with high thermal conductivity such as aluminum alloy, stainless steel or low carbon steel.

The working principle of the present invention is as follows.

After placing the required experimental items in the hanging basket of the high-speed rotor, close all doors and lifting hole valves of the entire vacuum chamber, open the valves of the air inlet and outlet pipes, and turn on the cold air cooling system; at the same time, open the upper collecting pipe and the valve of the lower header, open the refrigeration unit, open the cylindrical cooling device and the top annular cooling device, and turn on the main unit of the ultra-high gravity centrifuge and start working. When the temperature in the vacuum chamber rises to 40 degrees, if there is still an upward trend, close the air cooling system, open the vacuum exhaust pipe valve, and open the vacuum pump to vacuum. At this time, the cylindrical cooling device and the top annular cooling device continue to work. When the temperature in the cavity no longer rises, stop the vacuum pump and keep working under vacuum. When the temperature continues to drop below 20 degrees, you can adjust the vacuum degree or adjust the liquid output of the refrigerator to control the temperature in the vacuum chamber to work between 20-45 degrees.

When the main engine needs to stop, turn off the vacuum pump, open the re-pressure valve, turn off the refrigerator, turn off the cylindrical cooling device and the top ring cooling device, open the side door, and take out the test piece. The experiment is over.

What is claimed is:

1. A vacuum chamber structure of an ultra-high gravity geotechnical centrifuge device, comprising: a cylindrical shell (10), a convex head (19), a bottom head (7), a lower bearing sealing cover (4), and a vacuum pressure-bearing chamber formed by sealing a top cylindrical cylinder (24) and an upper sealing plate (22) with a first group of sealing rings (231) and a second group of sealing rings (232);

wherein a high-speed rotor system (46) is enclosed in the vacuum pressure-bearing chamber, and a cylindrical cooling device (11) is installed between an internal side of the cylindrical shell (10) and the high-speed rotor system (46), and a lower end of the main shaft (12) of the high-speed rotor system (46) extends through the lower bearing sealing cover (4) and a lower bearing system (3), extends out of the bottom head (7), and respectively connects a coupling (2) and a motor (1), in such a manner that the lower bearing system (3), the coupling (2) and the motor (1) are isolated from the vacuum chamber structure;

wherein an upper end of the main shaft (12) of the high-speed rotor system (46) passes through the upper sealing plate (22) and an upper bearing system (18) to connect an instrument compartment (25) installed in the top cylindrical cylinder (24);

in such a manner that the upper bearing system (18) and the instrument compartment (25) in the top cylindrical cylinder (24) at the center of the convex head (19) are isolated from the vacuum chamber structure;

wherein an upper bearing system support device (26) is a radial support structure formed by an upper bearing support ring (33) and multiple beams (32); a first end of each of the multiple beams (32) is connected to the upper bearing support ring (33), and a second end of each of the multiple beams (32) passes through the cylindrical shell (10) and is connected to a connecting backing plate (45); the connecting backing plate (45) is then connected to a side concrete (8), the upper bearing system (18) is installed in the upper bearing support ring (33); the first end of each of the multiple beams (32) is surrounded by a beam vibration isolation device (30), a cross-opening of a periphery of the second end of each of the multiple beams (32) and the cylindrical shell (10) is a clearance fit with beam passing, each of the multiple beams (32) is connected in seal with the cylindrical shell (10) via the beam vibration isolation device (30) and a first group of gasket (48);

wherein hanging baskets (13) are respectively provided on both sides of a rotating arm (14) of the centrifuge in the high-speed rotor system (46), and an annular cooling device (27) is provided on each of the multiple beams (32) directly above the hanging basket (13);

the cylindrical shell (10) is provided with multiple side wall connection pipes (51) and a side door (52); the convex head (19) is provided with a vacuum exhaust pipe (21), a lifting hole (29), an air intake pipe (34), a vacuum recompression pipe (35); and a spare connection pipe (53);

the cylindrical cooling device (11) and the annular cooling device (27) are connected and communicated with an upper liquid collecting pipe (28) and a lower liquid collecting pipe (9), and the upper liquid collecting pipe (28) passes through the cylindrical shell (10) to connect a low-temperature outlet of a refrigerator, and the lower liquid collecting pipe (9) passes through the cylindrical shell (10) to connect a return water inlet of the refrigerator; and a side door (52) is opened on a side of the cylindrical shell (10).

2. The vacuum chamber structure of the ultra-high gravity geotechnical centrifuge device, as recited in claim 1, wherein the top cylindrical cylinder (24) is provided with one or more U-shaped or Ω-shaped vibration isolation devices (20) in a middle of a body of the top cylindrical cylinder (24), and an upper end of the top cylindrical cylinder (24) and the convex head (19) is connected with the first group of sealing rings (231) through a block flange (50), the lower end of the top cylindrical cylinder (24) is connected with the upper bearing support ring (33) through the second group of sealing rings (232), and a bottom of the upper bearing support ring (33) is sealed and connected with the upper sealing plate (22), the upper sealing plate (22) is dynamically sealed and connected with the main shaft (12).

3. The vacuum chamber structure of the ultra-high gravity geotechnical centrifuge device, as recited in claim 1, wherein the beam vibration isolation device (30) comprises a beam cylindrical sleeve (54) and one or more U-shaped or Ω-shaped vibration isolation expansion joints (47) installed in a middle of a body of the beam cylindrical sleeve (54); a first end of the beam vibration isolation device (30) is welded or connected to the multiple beams (32) through the first group of gaskets (48), and a second end of the beam vibration isolation device (30) is connected to the cylindrical shell (10) through a second group of gasket (57).

4. The vacuum chamber structure of the ultra-high gravity geotechnical centrifuge device, as recited in claim 1, wherein the cylindrical cooling device (11) comprises multiple arc-shaped cooling units assembled into a complete circular cylinder, and each of the multiple arc-shaped cooling units comprises an upper side plate (38), a liquid inlet pipe (39) welded to the upper plate (38), a lower side plate (55), an outer arc plate (36), an inner arc plate (37), a left side plate (43), a right side plate (41) and an outlet pipe (44) welded to the lower side plate (55) which form a closed cavity; wherein the upper side plate (38), the lower side plate (55), the left side plate (43), and the right side plate (41) are in shapes of arc-shaped partitions, all of which are plates with an external convex arc-shape and an inner concave arc-shape; the outer arc plate (36) and the inner arc plate (37) are welded to the left side plate (43) and the right side plate (41) by a plurality of curved baffles (40), forming an S-shaped flow path (42); the liquid inlet pipe (39) is connected and communicated with the upper liquid collecting pipe (28), and the outlet pipe (44) is connected and communicated with a lower liquid collecting pipe (9); an annular cooling device (27) comprises several segment of ring cooling units (56), which form a complete circular ring plate.

5. The vacuum chamber structure of the ultra-high gravity geotechnical centrifuge device, as recited in claim 1, wherein the bottom head (7) is welded or riveted and fixed on a bottom concrete (6) by a tie bar (5) embedded in the bottom concrete (6); the bottom head (7) is welded to a bottom end of the cylindrical shell (10) to form one body.

6. The vacuum chamber structure of the ultra-high gravity geotechnical centrifuge device, as recited in claim 1, wherein the upper bearing system (18) is supported by the upper bearing support ring (33) and the multiple beams (32) with a first end fixed on the upper bearing support ring (33) and a second end connected with a connecting backing plate (45), and the connecting backing plate (45) is fixed on the side concrete (8).

7. The vacuum chamber structure of the ultra-high gravity geotechnical centrifuge device, as recited in claim 1, wherein materials of the cylindrical cooling device (11) and the annular cooling device (27) are aluminum alloy, stainless steel or low carbon steel.

* * * * *